United States Patent [19]

Agouridas et al.

[11] Patent Number: 5,089,476
[45] Date of Patent: Feb. 18, 1992

[54] GLUTAMIC ACID DERIVATIVES

[75] Inventors: Constantin Agouridas, Paris; Patrick Fauveau, Livry-Gargan; Chantal Damais, Paris, all of France

[73] Assignee: Roussel Uclaf, France

[21] Appl. No.: 161,163

[22] Filed: Feb. 26, 1988

[30] Foreign Application Priority Data

Feb. 26, 1987 [FR] France .................. 87 02547

[51] Int. Cl.$^5$ .............. A61K 37/02; C07K 5/06; C07K 5/08; C07K 5/10
[52] U.S. Cl. ...................... 514/18; 514/19; 530/330; 530/331
[58] Field of Search ............ 530/330, 331; 514/18, 514/19

[56] References Cited

U.S. PATENT DOCUMENTS 4,311,640  1/1982  Kuroda et al. .................. 530/332
4,730,006  3/1988  Bohme et al. .................. 514/19

*Primary Examiner*—Lester L. Lee
*Attorney, Agent, or Firm*—Bierman and Muserlian

[57] ABSTRACT

All isomeric forms and mixtures of isomers of glutamic acid compounds of the formula

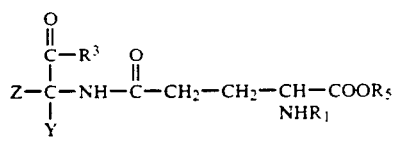

wherein the glutamic aid is of D- or L- configuration, $R_1$ is selected from the group consisting of hydrogen, alkyl of 1 to 5 carbon atoms, an amino acid, a peptide of 2 to 4 amino acids and an amino acid or a peptide of 2 to 4 amino acids in which the amine is esterified with an optionally unsaturated aliphatic carboxylic acid of 6 to 24 carbon atoms or $R_1$ is selected from the group consisting of a residue of a $C_6$-$C_{24}$ optionally unsaturated aliphatic acid. $R_5$ is selected from the group consisting of hydrogen or an alkyl radical of 1 to 5 carbon atoms, $R_3$ is selected from the group consisting of hydroxy, alkoxy of 1 to 5 carbon atoms, an amino acid with the amine optionally substituted with alkyl of 1 to 5 carbon atoms, Z is

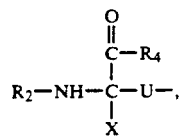

$R_2$ is selected from the group consisting of hydrogen, an amino acid and a peptide of 2 to 4 amino acids. $R_4$ is selected from the group consisting of hydroxy, alkoxy 1 to 5 carbon atoms and an amino acid optionally substituted on the amine with alkyl of 1 to 5 carbon atoms, U is selected from the group consisting of

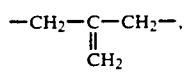

—CH═CH—CH$_2$— (E or Z isomer), —CH$_2$—CH═CH— (E or Z isomer) and

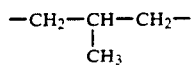

or U and Y together are ═CH—CH$_2$—CH$_2$— (E or Z isomer) and X is hydrogen and their salts with non-toxic, pharmaceutically acceptable acid or bases having immunomodulatory properties.

18 Claims, No Drawings

GLUTAMIC ACID DERIVATIVES

STATE OF THE ART

French Patent No. 2,566,410 describes diaminopimelic acid compounds having antibacterial properties and U.S. Pat. No. 4,311,640 describes related compounds.

OBJECTS OF THE INVENTION

It is an object of the invention to provide the novel compounds of formula I and their non-toxic, pharmaceutically acceptable addition salts and a process for their preparations.

It is another object of the invention to provide novel immunomodulating compositions and a novel method of inducing immunomodulating activity in warm-blooded animals.

These and other objects and advantages of the invention will become obvious from the following detailed description.

THE INVENTION

The novel compounds of the invention are selected from the group consisting of all isomeric forms and mixtures of isomers of glutamic acid compounds of the formula

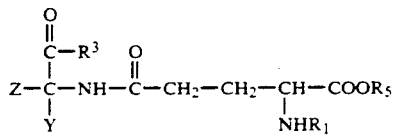

wherein the glutamic acid is of D- or L- configuration, $R_1$ is selected from the group consisting of hydrogen, alkyl of 1 to 5 carbon atoms, an amino acid, a peptide of 2 to 4 amino acids and an amino acid or a peptide of 2 to 4 amino acids in which the amine is esterified with an optionally unsaturated aliphatic carboxylic acid of 6 to 24 carbon atoms or $R_1$ is selected from the group consisting of a residue of a $C_6$-$C_{24}$ optionally unsaturated aliphatic acid. $R_5$ is selected from the group consisting of hydrogen and an alkyl of 1 to 5 carbon atoms, $R_3$ is selected from the group consisting of hydroxy, alkoxy of 1 to 5 carbon atoms and an amino acid with the amine optionally substituted with alkyl of 1 to 5 carbon atoms, Z is

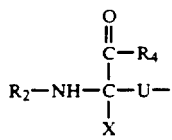

$R_2$ is selected from the group consisting of hydrogen, an amino acid and a peptide of 2 to 4 amino acids, $R_4$ is selected from the group consisting of hydroxyl, alkoxy of 1 to 5 carbon atoms and an amino acid optionally substituted on the amine with alkyl of 1 to 5 carbon atoms, U is selected from the group consisting of

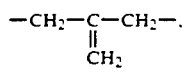

—CH=CH—CH$_2$— (E or Z isomer), —CH$_2$—CH=CH— (E or Z isomer) and

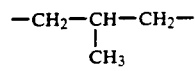

or U and Y together are =CH—CH$_2$—CH$_2$— (E or Z isomer) and X is hydrogen or U and X together are =CH—CH$_2$—CH$_2$— (E or Z isomer) and Y is hydrogen and their salts with non-toxic, pharmaceutically acceptable acid or bases.

The amino acid in the compounds of formula I is preferably an α-amino acid and examples of such acids are Ala, Val, Ival, Leu, Ile, Asp, Asn, Glu, Gln, Ser, Thr, Cys, Met, Lys, Arg, Phe, Tyr, Trp, His and Pro, Nva, Nle, Hyp, Orn, in the D or L form, as well as Sar and Gly, it being possible for all the said acids to be N-esterified or N-alkylated. In the case of a peptide of 2,3 or 4 amino acids, the latter is chosen from the group consisting of the above amino acids. It will be understood by convention that the symbols for the -amino carboxylic acids denote these acids in their D or L configuration (for example, the term Ala denotes alanine in D form or in L form).

The saturated or unsaturated aliphatic acid of 6 to 24 carbon atoms, preferably from 12 to 22 carbon atoms, may be stearic acid, palmitic acid, lauric acid, caprylic acid, myristic acid, α- or γ-linolenic acid, linoleic acid, arachidonic acid or docosapentaenoic acid.

Examples of alkyl of 1 to 5 carbon atoms are pentyl, isobutyl, butyl and isopropyl, and preferably propyl, ethyl or methyl. Examples of alkoxy of 1 to 5 carbon atoms are pentoxy or butoxy, but preferably propoxy, ethoxy or methoxy.

The products of formula I contain one or more asymmetric carbon atoms and, as stated above, the subject of the invention is the said compounds of formula I in all their possible isomeric forms and in the form of mixtures.

The non-toxic, pharmaceutically acceptable salts of the derivatives of the invention can be formed with organic and inorganic bases such as alkali metal and alkaline earth metal hydroxides such as, for example, sodium, potassium, lithium and calcium hydroxides, and magnesium or ammonium hydroxide. Among organic bases, there may be mentioned substituted or unsubstituted alkylamines such as trimethylamine, methylamine, propylamine, N,N-dimethylethanolamine or tris(hydroxymethyl)methylamine. Basic amino acids such as lysine or arginine may also be mentioned as well as glucosamine or procaine may be mentioned.

The addition salts with inorganic or organic acids can be, for example, the salts formed with hydrochloric acid, hydrobromic acid, nitric acid, sulfuric acid, phosphoric acid, acetic acid, formic acid, propionic acid, maleic acid, fumaric acid, succinic acid, tartaric acid, citric acid, oxalic acid, glyoxylic acid and aspartic acid, alkanesulfonic acids such as methane- and ethanesulfonic acid, arylsulfonic acids such as benzene- or p-toluenesulfonic acid, and arylcarboxylic acids such as benzoic acid.

Among the preferred compounds of formula I are those wherein the glutamic acid has the D-configuration, those wherein $R_3$ and $R_4$ are hydroxy, those wherein $R_5$ is hydrogen and their non-toxic, pharmaceutically acceptable acid addition salts. Specific preferred compounds are 2-amino-6-γ-D-glutamylamino)-

4-methyleneheptanedioic acid and 2-(L-alanylamino)-6-(γ-D-glutamylamino)-4-methyleneheptanedioic acid, and their non-toxic, pharmaceutically acceptable acid addition salts.

The novel process of the invention for the preparation of the compounds of formula I comprises reacting a glutamic acid compound of the formula

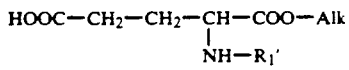

wherein Alk is alkyl of 1 to 3 carbon atoms and $R'_1$ has the definition of $R_1$ other than hydrogen or an amino protective group with a compound of the formula

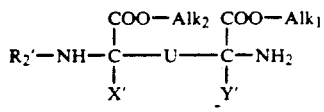

as an isomer or mixture of isomers wherein U has the above definition, Alk and $Alk_2$ are alkyl of 1 to 3 carbon atoms, X' and Y' are hydrogen or —$COOAlk_3$, $Alk_3$ is alkyl of 1 to 3 carbon atoms or together with U form an additional bond and $R'_2$ is amine protecting group, an amino acid or a peptide of 2 to 4 amino acids with the amine protected to obtain a compound of the formula

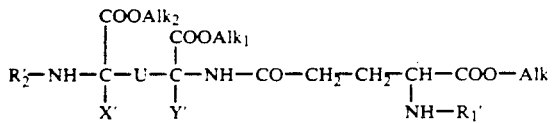

in all isomeric forms or isomeric mixtures which is optionally isolated and salified or subjected to the following reactions in any order:

a) if X' or Y' is COO—$Alk_3$: decarboxylation,
b) deprotection of the amino groups,
c) dealkylation of the hydroxyl groups,
d) amidation of the free amino groups with an amino acid or a peptide of 2,3 or 4 amino acids in which the amino group is protected, followed by deprotection of this amino group,
e) esterification or salification of the carboxy groups with a base, and
f) salification of the amino groups with an acid.

In a preferred mode of the process of the invention, the glutamic acid compound of formula II is activated by formation of a mixed anhydride such as with isobutyl chloroformate or by the presence of a condensation agent such as dicyclohexylcarbodiimide, N,N'-carbonyldiimidazole or bis(alkylamides) of sulfurous acid such as

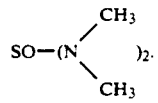

The decarboxylation is preferably effected with a concentrated inorganic acid such as 12N hydrochloric acid. A direct decarboxylation may be effected directly by the procedure of Krapcho or Keinan et al [J. Org. Chem., Vol. 51 (1986), p.3615-3619].

The deprotection of the amino groups (formyl or BOC, for example) is preferably carried out with a dilute mineral acid such as hydrochloric acid. The dealkylation of the carboxyl groups is preferably carried out by saponification with an inorganic base such as potassium hydroxide and, preferably sodium hydroxide. It can, if necessary, be performed in two steps in the event of being incomplete. In the latter case, the second dealkylation is preferably carried out after the deprotection of the amino groups and/or the decarboxylation. The amidation of the free amino groups is carried out, for example, using a functional derivative such as a halide of the amino acid or peptide, or in the presence of a condensation agent such as those mentioned above. The esterification of the carboxyl groups is carried out, for example, under the same conditions as above (condensing agents).

The compounds of formula I may have a basic or acidic nature and if so, the addition salts thereof may be prepared by reaction with the appropriate base or acid in substantially stoichiometric form.

In a preferred embodiment of the process, the compound of formula $I_A$ is subjected to the following reactions: dealkylation of the carboxyl groups, deprotection of the amino groups and decarboxylation, amidation or salification of the amino groups with an acid and/or esterification or salification of the carboxyl groups with a base.

Some of the compounds of formula III are known and if they are not known, they may be prepared by reacting a compound of the formula

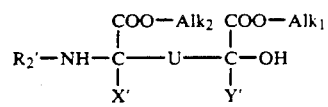

wherein $Alk_1$, $Alk_2$, U, X', Y' and $R'_2$ have the above definitions with an alkanesulfonyl halide of 1 to 3 alkyl carbon atoms, preferably methane sulfonyl chloride, in the presence of a condensation agent such as pyridine and then with an alkali metal azide such as sodium azide or diphenylphosphoryl azide to form a compound of the formula

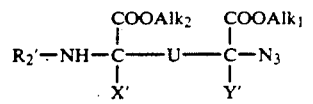

reducing the latter with triphenyl phosphine, for example, followed by aqueous hydrolysis or by catalytic hydrogenation in the presence of a Lindlar catalyst (poisoned palladium or charcoal) to form a compound of the formula

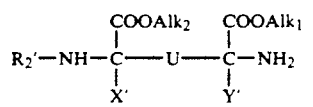

wherein $R_2$, X', Y', U, $Alk_1$ and $Alk_2$ have the above definitions and when X' and/or Y' are other than hydrogen, reacting the latter an agent to protect the amino group to form a compound of the formula

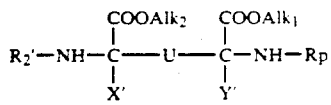

wherein $R_2$, $Alk_1$, $Alk_2$, U, X' and Y' have the above definitions and Rp is an amino protective group, subjecting the latter to a decarboxylating agent to obtain the corresponding compound with 1 or 2 asymetrical carbon atoms, separating the latter into the isomers or diastereoisomers such as by crystallization or chromatography and then removing the amino protective group to form the compound of formula III in the form of separate isomers or isomeric mixtures.

The compounds of formulae II and IV are known.

The novel immunomodulatory compositions of the invention are comprised of an immunomodulatorily effective amount of at least one compound of formula I and its non-toxic, pharmaceutically acceptable salts with acids and bases and an inert pharmaceutical carrier or excipient. The compositions may be in the form of tablets, dragees, gelatin capsules, granules, suppositories and injectable solution or suspensions.

Examples of suitable excipients are talc, gum arabic, lactose, starch, magnesium stearate, cocoa butter, aqueous or non-aqueous vehicles, fats of animal or vegetable origin, paraffinic derivatives, glycols, the various wetting, dispersing or emulsifying agents and preservatives.

The compositions of the invention have exceptional immunomodulatory properties, particularly by activation of human monocytes and production of monokines such as TNF (tumor necrosis factor) and IL-1, interleukin-1.

They are useful in the treatment of autoimmune diseases, whether conditions affecting organs nonspecifically (rheumatoid polyarthritis, lupus erythematosus, haemolytic anaemia, autoimmune leukopenia, and the like) or specific diseases of organs (thyroiditis, Basedow's disease, Addison's disease, multiple sclerosis, pemphigus, haemorrhagic rectocolitis, some types of nephropathy, and the like). Compositions are also be useful in the treatment of haemopathies, cancer, AIDS, viral and microbial conditions, especially those which are chronic and recurrent (bronchitis, influenza, and the like), diseases of the oral cavity, and the like. They can constitute adjuvants of viral therapy, antibiotic therapy or anticancer chemotherapy.

The compositions also find use in the treatment of many secondary or acquired immune deficiency states observed during a wide variety of conditions: deficiencies associated with metabolic disorders, deficiencies of iatrogenc origin (corticoids, ionizing radiation, etc.), deficiencies observed in major burns patients, and the like.

The novel method of the invention for inducing immunodulatory activity in warm-blooded animals, including humans, comprises administering to warm-blooded animals an immunodulatorily effective amount of at least one compound of formula I and its non-toxic, pharmaceutically acceptable salts with acids and bases. The compounds may be administered orally, rectally or parenterally and the usual daily dose is 0.007 to 0.7 mg/kg depending on the compound, condition treated and method of administration. For example, the compound of Example may be orally administered at a dose 0.007 to 0.7 mg/kg for the treatment of rheumatoid polyarthritis.

In the following examples there are described several preferred embodiments to illustrate the invention. However, it is to be understood that the invention is not intended to be limited to the specific embodiments.

EXAMPLE 1

2-amino-6-($\gamma$-D-glutamylamino)-4-methylene-heptanedioic acid .

STEP A: Triethyl 1-formylamine-3-methylen-5-[(N-trifluoroacetyl-O-methyl-$\gamma$-D-glutamyl)-amino-1,1,5-pentanetricarboxylate A solution of 4 g of 1-methyl N-trifluoroacetyl-D-glutamate in 20 ml of dimethoxyethane was added to a solution of 5.1 g of triethyl 5-amino-1-(formylamino)-3-methylene-1,1,5-pentanetricarboxylate in 280 ml of dimethylethylamine and the mixture was cooled to 0° C. 3.2 g of dicyclohexylcarbodiimide were added in small portions and the mixture was stirred for 16 hours at 0° C. and filtered. The filtrate was evaporated to dryness and the residue was taken up with cold dimethoxyethane. The mixture was filtered and the filtrate was taken to dryness. The residue was taken up in methylene chloride and the mixture was washed with N hydrochloric acid, with saturated sodium bicarbonate solution and then with water saturated with sodium chloride, dried and evaporated to dryness. The residue was purified by chromatography on silica (eluant:ethyl acetate/cyclohexane 5:5) to obtain 5 g of the expected product with a specific rotation of $[\alpha]_D = +8$ (c=1% in methylene chloride).

STEP B:

2-amino-6-($\gamma$-D-glutamylamino)-4-methylene-heptanedioic acid

Saponification:
10.9 ml of N sodium hydroxide were added dropwise over 5 minutes at 0° C. to a solution of 1.28 g of the product Step A in 20 ml of ethanol and the mixture was allowed to return to room temperature and stirred for 24 hours. It was neutralized with 0.9 ml of 12N hydrochloric acid and taken to dryness under reduced pressure.

Decarboxylation - deformylation:
The residue was taken up in 10 ml of ethanol and 1 ml of 12N hydrochloric acid was added and the mixture was stirred for 40 minutes at 80° C.

Saponification:
The above product was chilled and 15.2 ml of 2N sodium hydroxide were added dropwise over 5 minutes. The mixture was stirred for 24 hours at room temperature, brought to pH 6 using 12N hydrochloric acid and taken to dryness.

Purification:
The above product was taken up in a few ml of water and the pH was adjusted to 6 with N sodium hydroxide. The mixture was dealkalinized on Dowex 50 W×8 H+ resin (50–100 mesh) and elution was performed first with water and then with N ammonia solution. The product was purified by chromatography on silica (eluant: ethanol/ammonia solution 95:5, then ethanol/ammonia solution 8:2) and the eluate was evaporated to dryness. The residue was taken up in 200 ml of water and the mixture was filtered. The filtrate was lyophilized for 16 hours to obtain 400 mg of the expected product with a specific rotation $[\alpha]_D = -9.5° \pm 1°$ (c=1% in 4N hydrochloric acid).

A) Preparation of 1-methyl-N-trifluoroacetyl-D-glutamate

STEP 1: 5-(1,1-dimethylethyl)-N-trifluoroacetyl-D-glutamate 4.1 ml of triethylamine and then, while cooling 4.1 ml of trifluoroacetic anhydride were added dropwise to a solution of 5.5 g of 5-(1,1-dimethylethyl)-1-methyl-D-glutamate in 180 ml of methylene chloride. The mixture was then stirred for 2 hours at room temperature and poured into 70 ml of ice-cold water. The resulting mixture was extracted with methylene chloride and the extract was washed with saline solution, dried and taken to dryness to obtain 7.1 g of the expected product with a specific rotation of $[\alpha]_D = +5° \pm 1°$ (c=1.3% in dioxane).

STEP 2: 1-methyl-N-trifluoroacetyl-D-glutamate 6.8 g of the product of Step 1 were dissolved in 50 ml of methylene chloride and 50 ml of trifluoroacetic acid were added. The mixture was stirred for 1 hour and evaporated to dryness. The residue was taken up in ethyl acetate and the mixture was poured into water. The resulting mixture was extracted with ethyl acetate and the extract was washed with saline solution and taken to dryness to obtain 5.5 g of the expected product with specific rotation of $[\alpha]_D = +9° \pm 2°$ (c=0.6% in dioxane)

B) Preparation of the starting triethyl 5-amino-1-(formylamino)-3-methylene-1,1,5-pentanetricarboxylate

STEP 1: Diethyl 2-(formylamino)-(2-methyl-2-propenyl)-propanedioate 40 g of potassium carbonate, 0.380 g of 18-crown-6-crown ether catalyst and 39.9 g of chloromethylpropene were added to a solution of 30 g of ethyl formamidomalonate in 300 ml of cyanomethyl and the mixture was stirred at reflux for 3 hours and filtered. The filtrate was evaporated to dryness and the residue was cooled to 0° C. to 5° C. and taken up in 10 ml of isopropyl ether. The mixture was filtered, washed with isopropyl ether and dried under reduced pressure to obtain 25.2 g of the expected product with a melting point of 72° C.

STEP 2: Triethyl 1-(formylamino)-5-hydroxy-3-methylene-1,1,5-pentanetricarboxylate (mixture of isomers)

A solution of 26.5 g of ethyl glyoxylate in 180 ml of methylene chloride was added dropwise over 10 minutes to a solution of 84 g of ferric chloride in 180 ml of methylene chloride and the mixture was stirred for 1 hour and cooled to −20° C. A solution of 34 g of the product of Step A in 180 ml of methylene chloride was added dropwise over 20 minutes, and the mixture was stirred for 1 hour at −20° C. and was then poured into 300 ml of ice-cold water. The resulting mixture was extracted with methylene chloride and the extract was washed with 2N HCl and then with saline solution, dried and evaporated to dryness under reduced pressure to obtain 56.5 g of the expected product (mixture of isomers) with a melting point of 68° C. after purification by chromatography on silica (eluant:ethyl acetate/cyclohexane 6:4).

STEP 3: Triethyl 5-azido-1-(formylamino)-3-methylen-1,1,5-pentanetricarboxylate 46 g of the product (mixture of isomers) of Step 2 were dissolved in 500 ml of pyridine and the mixture was cooled to 0° C. 12 ml of methanesulfonyl chloride were added dropwise at 0° C. and the mixture was stirred for 3 hours at room temperature and poured into 400 ml of ice-cold 4N hydrochloric acid and 200 ml of methylene chloride. The resulting mixture was extracted with methylene chloride and the extract was washed with 4N hydrochloric acid, with saturated sodium bicarbonate solution and with saline solution, dried and evaporated to dryness under reduced pressure. The 56 g of residue obtained were dissolved in 250 ml of dimethylformamide and 9.98 g of sodium azide were added. The mixture was stirred for 16 hours at room temperature and the solvent was removed. The residue was taken up in methylene chloride and the mixture was washed with saturated sodium bicarbonate solution and then with saline solution, dried and taken to dryness to obtain 59 g of expected product (mixture of isomers) which was purified by chromatography on silica (eluant:cyclohexane/ethyl acetate 8:2) to obtain 26 g of the expected product.

STEP 4: Triethyl 5-amino-1-(formylamino)-3-methylene-1,1,5-pentanetricarboxylate 10.9 g of triphenylphosphine were added to a solution of 13 g of the product of Step 3 in 250 ml of tetrahydrofuran at approximately −5° C. and the mixture was stirred for 5 hours at room temperature. 8.5 ml of water were added and the mixture was stirred for 24 hours at room temperature. The tetrahydrofuran was evaporated off and the residue was taken up in methylene chloride. The mixture was poured into ice-cold 2N hydrochloric acid, followed by extraction with 2N hydrochloric acid, neutralization with sodium bicarbonate and extraction with methylene chloride. The extract was washed with saline solution, dried and evaporated to dryness to obtain 10 g of the expected product melting at 50° C. after crystallization from isopropyl ether.

EXAMPLE 2

2-(L-Alanylamino)-6-(γ-D-glutamylamino)-4-methyleneheptanedioic acid

STEP A: Triethyl 1-amino-3-methylene-5-(N-trifluoroacetyl-0-methyl-γ-D-glutamyl)-amino]-1,1,5-pentanetricarboxylate 1.5 ml of 12N hydrochloric acid were added to a solution of 1.22 g of product of Step A of Example 1 in 15 ml of ethanol and the mixture was stirred for 40 minutes at 80° C. The solvent was removed under reduced pressure and the residue was taken up in 10 ml of water. The mixture was neutralized with sodium bicarbonate and extracted with methylene chloride. The extract was washed with saline solution, dried and taken to dryness. The residue was purified by chromatography on silica (eluant:ethyl acetate/cyclohexane 8:2) to obtain 0.850 g of the expected product.

STEP B: Triethyl 1-
N-[(1,1-dimethylethoxy)-carbonyl]-L-alanylamino
-3-methylene-5-[(N-trifluoroacetyl-0-methyl-γ-D-
glutamyl)amino]-1,1,5-pentanetricarboxylate 0.310 g of BOC-L-alanine were dissolved in 50 ml of tetrahydrofuran and 0.43 ml of triethylamine were added. The mixture was cooled to approximately 5° C. and 0.23 ml of isobutyl chloroformate were added. The mixture was stirred for 30 minutes at approximately +5° C. and a solution of 0.800 g of the product of Step A in 10 ml of tetrahydrofuran was added dropwise over 5 minutes. The mixture was allowed to return to room temperature and was stirred for 16 hours. The tetrahydrofuran was removed and the residue was taken up in a water/methylene chloride mixture. The mixture was extracted with methylene chloride and the extract was washed with saline solution, dried and taken to dryness. The residue was purified by chromatography on silica (eluant: ethyl acetate/cyclohexane 5:5) to obtain the expected product with a specific rotation of $[\alpha]_D = 12° \pm 1°$ (c=1% in methylene chloride).

STEP C:
2-L-alanylamino)-6-(γ-D-glutamylamino)-4-
methyleneheptanedioic acid

Using the procedure of Step B of Example 1, 700 mg of the product of Step B were reacted. Saponification, deprotection of the BOC-protected amine, saponification and purification were performed to obtain 170 mg of the expected product with a specific rotation of $[\alpha]_D = -13° \pm 1°$ (c=1% in 4N HCl).

EXAMPLE 3

2-amino-4-methylene-6-[N-1-oxooctadecyl)-L-alanyl-γ-
D-glutamylamino]-heptanedioic acid Using the procedure of Example 1, 1-methyl N-[N-(1-oxooctadecyl)-1-alanyl]-D-glutamate was used in place of the corresponding N-trifluoroacetyl derivative obtained in the preparation A of Example 1, to obtain the expected product with a specific rotation of $[\alpha]_D = -25°$ (c=0.6% in water).

Preparation of 1-methyl
N-[N-(1-oxooctadecyl)-L-alanyl]-D-glutamate

STEP 1: Methyl N-(1-oxooctadecyl)-L-alaninate 24.9 ml of triethylamine were added to a solution of 10 g of 1-alanine methyl ester hydrochlorde in 250 ml of methylene chloride, followed, by dropwise addition over 30 minutes of a solution of 21.7 g of stearyl chloride in 50 ml of methylene chloride. The mixture was stirred for 150 minutes and filtered and the filtrate was washed with 2N hydrochloric acid, then with saline solution, dried and taken to dryness under reduced pressure. The residue was made into a paste with isopropyl ether, vacuum filtered and crystallized in methanol to obtain 22 g of the expected product with melting point of 84° C. and with a specific rotation of $[\alpha]_D = -15°$ (c=1%, pyridine)

STEP 2: N-(1-oxooctadecyl)-L-alanine

A suspension of 21 g of above product in 500 ml of methanol was cooled to 0° C. and 62 ml of N potassium hydroxide were added dropwise. The mixture was stirred for 16 hours at room temperature and 500 ml of methanol were added. The mixture was stirred for 4 hours, cooled to 0° C., brought to a pH of 3 using 2N hydrochloric acid and evaporated. The residue was taken up in methylene chloride and the mixture was washed with saline solution, dried and taken to dryness under reduced pressure. The residue was made into a paste with isopropyl ether vacuum filtered and crystallized from methanol to obtain 11.8 g of the expected product melting at 102° C. and having a specific rotation of $[\alpha]_D = -18°$ (c=0.9% in pyridine).

STEP 3: 5-(1,1-dimethylethyl) 1-methyl
N-[N-(1-oxooctadecyl) -L-alanyl]-D-glutamate A suspension of 1.77 g of N-(1-oxooctadecyl)-L-alanine and 1.08 g of 5-(1,1-dimethylethyl)-1-methyl D-glutamate in 170 ml of dimethoxyethane was cooled to 0° C. and a solution of 1.23 g of N,N-dicyclohexylcarbodiimide in 5 ml of dimethoxyethane was added dropwise over 10 minutes. The mixture was stirred for 3 hours at room temperature, cooled and filtered. The filtrate was evaporated to dryness and the residue was taken up in 250 ml of ether in the heated state. The mixture was filtered and the filtrate was evaporated to dryness under reduced pressure. The residue was made into a paste in isopropyl ether and vacuum filtered to obtain 2.4 g of the expected product melting at $\approx 100°$ C. after crystallization in methanol and having a specific rotation of $[\alpha]_D = -32° \pm 1°$ (c=1% in CH$_2$Cl$_2$).

STEP 4: 1-Methyl
N-[N-(1-oxooctadecyl)-L-alanyl]-D-glutamate 31 ml of trifluoroacetic acid were added dropwise to a solution of 11.4 g of the product of Step 3 in 150 ml of methylene chloride and the mixture was left for 16 hours with stirring and then evaporated to dryness under reduced pressure. The residue was taken up in methylene chloride and the mixture was washed with saline solution, dried and filtered. The filtrate was evaporated to dryness under reduced pressure and the residue was then crystallized from ethanol to obtain 6.8 g of the expected product melting at $\approx 100°$ C. and having a specific rotation of $[\alpha]_D = -16° \pm 1°$ (c=0.9% in pyridine).

EXAMPLE 4

2-Amino-6-(γ-D-glutamylamino)-3-heptenedioic acid

Using the procedure of Example 1, triethyl 5-amino-1-formylamino-2-pentene-1,1,5-tricarboxylate was reacted to obtain the expected product.

Preparation of trietyl
5-amino-1-formylamino-2-pentene-1,1,5-tricarboxylate

Using the procedure for the preparation of triethyl 5-amino-1-(formylamino)-3-methylene-1,1,5-pentanetricarboxylate, chloro-methylpropene replaced the allyl bromide to obtain the expected product in the form of an oil with an Rf=0.4 in ethyl acetate/ethanol 4:1.

EXAMPLE 5

2-Glycylamino-6-
[N-(1-oxododecyl)-L-alanyl-γ-D-glutamyl]-amino-2-
heptenedioic acid Using the procedure of Example 1, 1-methyl N-[N-(1-oxododecyl)-L-alanyl]-D-glutamate [prepared like 1-methyl N-[N(1-oxooctadecyl)-L-alanyl]-D-glutamate in Example 3 by replacing stearyl by lauryl (dodecyl)] was reacted with 7-ethyl 1-methyl 6-amino-2-[(N-formyl-glycyl)-amino]-3-heptenedioate. In this case, deformylation with hydrochloric acid was not necessary and the neutralization and the desalification were carried out simultaneously using a H+ resin (Amberlyst 15). The expected product, which became resinous at 150 C, was obtained and had a specific rotation of $[\alpha]_D = -14$ (c=0.8% in water).

EXAMPLE 6

Mixture of (2D, 6L)- and (2L, 6D)-2-amino-6-(γ-D-glutamylamino)-4-methyleneheptanedioic acid STEP A: Mixture of(2D, 6L)-and (2L, 6D)-2-formylamino-4-methylene -6-[N-(trifluoroacetyl)- -D-glutamylamino]-heptanedioic acids 1.3 g of dicyclohexylcarbodiimide were added at 0 C to a solution containing 1.5 g of the mixture of diethyl (2D,6L)- and (2L, 6D)-2-formamido-4-methylene-6-amino-1,7-heptanedioate and 1.48 g of D-glutamic acid in 150 ml of dimethoxyethane, and the resulting mixture was stirred for 16 hours while the temperature is maintained at 0° C. The precipitate was filtered off and the filtrate was concentrated to dryness under reduced pressure. The 10.5 g of crude product were purified by chromatography on silica (eluant:cyclohexane/ethyl acetate 2:8) to obtain the expected product with a specific rotation of $[\alpha]_D = -14°$ (c=0.8% in water).

STEP B: Mixture of (2D,6L)- and (2L,6D)-2-amino-6-(γ-D-glutamylamino)-4-methyleneheptanedioic acids 5 ml of 12N hydrochloric acid were added to 1.9 g of the product of Step A dissolved in 100 ml of ethanol, and the mixture was stirred for 30 minutes. The solvent was removed under reduced pressure and the residue was taken up in 50 ml of ethanol. The pH was adjusted to 7 with 0.1N sodium hydroxide solution and the mixture was cooled to 0° C. and 16 ml of N sodium hydroxide were added dropwise. The reaction medium was allowed to return to room temperature, stirred for 16 hours and neutralized with N hydrochloric acid. The solvents were removed under reduced pressure and the residue was chromatographed on silica (eluant:ethanol-/ammonia solution 95:5, 90:1 and then 80:20). The resin obtained was taken up in water and the mixture was filtered and the filtrate was lyophilized to obtain 0.92 g of expected product with a specific rotation of $[\alpha]_D = -13° \pm 1°$ (c=1% in 3N HCl).

EXAMPLE 7

Mixture of (2D, 6D), 6L)-2-amino-6-(γ-D-glutamylamino)-4-methyleneheptanedioic acids STEP A: Mixture of (2D, 6D)- and (2L,6L)-2-formylamino-4-methylene -6-[N-(trifluoroacetyl)-γ-D-glutamylamino]-heptanedioic acids Using the procedure of Step A of Example 6, a mixture of diethyl (2D,6D)- and (2L,6L)-2-formamido-4-methylene-6-amino-1,7-heptanedioates was reacted to obtain the expected product.

STEP B: Mixture of (2D,6D)- and (2L,6L)-2-amino-6-(γ-D-glut amylamino)-4-methyleneheptanedioic acids Using the procedure of Step B of Example 6, the product of Step A was reacted to obtain the expected product having a specific rotation of $[\alpha]_D = -12.5° \pm 1°$ (c=[lacuna], 3N HCl)

The mixture of diethyl (2D,6D)- and (2L,6L)-2-formamido-4-methylene-6-amino-1,7-heptanedioates used at the beginning of Example 7 was prepared as described in the preparation of the Example (Step C), starting with the mixture of diethyl (2D,6D)- and (2L,6L)-2-formamido-4-methylene-6-tert-butoxycarbonylamino-1,7-heptanedioates (isomer I) obtained in Step B of this preparation.

Preparation of 7-ethyl 1-methyl 6-amino-2-[(N-formylglycyl)amino]-3-heptenedioate Using the procedure of preparation B of Example 1, diethyl (formylamino)-(2-methyl-2-propenyl)-propanedioate in Step 2 was replaced by methyl 2-[(N-formylglycyl)-amino]-2-(2-propenyl)ethanoate to obtain the expected product with an Rf=0.2 in a methylene chloride/methanol (9:1) mixture.

Comment:

The reduction of the azide to amine (Step 4 of preparation B of Example 1) was carried out by hydrogenation in the presence of palladium on calcium carbonate and of quinoline, instead of triphenyl phosphine.

Preparation of the mixture of diethyl (2D,6L)- and (2L, 6D)-2-formamido -4-methylene-6-amino-1,7-heptanedioates STEP A: Triemethyl 1-formamido-3-methylene-5-(tertbutoxycarbonylamino)-1,1,5-pentanetricarboxylate 13.6 g of di-tert-butyl pyrocarbonate dissolved in 25 ml of methylene chloride were added at room temperature to 19.5 g of triethyl 1-formamido-3-methylene-5-amino-1,1,5-pentanetricarboxylate dissolved in 75 ml of methylene chloride, and the mixture was maintained with stirring at room temperature for 36 hours. The reaction medium was diluted with 150 ml of methylene chloride and the organic phase was washed with water and dried. The solvents were removed under reduced pressure and the mixture was left to crystallize at +4° C. to obtain 25.8 g of expected product melting at 68° C.

STEP B: Mixture of diethyl (2D,6D)- and (2L,6L-2-formamido-4-methylene -6-(tert-butoxycarbonylamino)-1,7-heptanedioates and mixture of (2D,6L) and (2L,6D) isomers 2.21 g of diethylcaesium and 9.42 g of p-aminophenol were added to 17.25 g of product of Step A dissolved in 250 ml of dimethylformamide, and the mixture was heated for 3 hours to 85° C. The mixture was allowed to return to room temperature and was filtered. The solvents were removed under reduced pressure and the residue was taken up in 300 ml of methylene chloride. The organic phase was washed with 0.5N hydrochloric acid and then with aqueous sodium bicarbonate solution and dried. The solvent was removed under reduced pressure and the residue was chromatographed on a silica column (eluant:cyclohexane/ethyl acetate 6:4) to obtain 4.70 g of isomer I (DD,LL isomer), 3.84 g of isomer 11 (DL,LD isomer) and 2.80 g of a mixture of the 2 isomers.

STEP C: Mixture of diethyl (2D,6L)- and (2L,6D)-2-formamido-4-methylene-6-amino-1,7-heptanedioates 25 ml of 2N hydrochloric acid in ether were added to 3 g of product II of Step B (DL,LD isomer) dissolved in 50 ml of methylene chloride. The mixture was stirred at room temperature for 30 minutes and concentrated under an inert atmosphere. The amine hydrochloride was taken up in methylene chloride to which triethylamine had been added, and the mixture was then evaporated to dryness under reduced pressure. After chromatography on silica (eluant:ethyl acetate/cyclohexane 7:3), 1.86 g of expected product were recovered.

EXAMPLE 8

Tablets were prepared containing 50 mg of 2-amino-6-(γ-D-glutamylamino)-4-methyleneheptanedioic acid and sufficient excipient of lactose, starch, talc, magnesium stearate for a final weight of 100 mg.

EXAMPLE 9

Tablets were prepared containing 50 mg of 2-(L-alanylamino)-6-(γ-D-glutamylamino)-4-methylene-heptanedioic acid and sufficient excipient of lactose, starch, talc, magnesium stearate for a final weight of 100 mg.

PHARMACOLOGICAL STUDY

Stimulation of monocytic cells with an immunostimulant

The mononuclear cells of the circulating blood of normal donors were separated by the classical technique described by Boyum using a Ficoll gradient. After being washed, the mononuclear cells were incubated at 37° C. for 1 hour in the proportion of $5 \times 10^6$ monocytes (NSE+ cells) per ml of culture medium, 5 ml per culture bottle. The culture medium used in this experiment was composed of RPMI 1640 to which antibiotics and HEPES buffer had been added. After one hour, the non-adherent cells were removed by washing the bottles with medium previously brought to 37 C, and the adherent cells, composed essentially of monocytes (>90%), were cultured again in the presence of different amounts of test products in a PBS medium (Dulbecco) without $Ca^{2+}$ or $Mg^{2+}$. Culturing was continued for 24 or 48 hours and the cell supernatants were then withdrawn, centrifuged, aliquoted and stored either at −80° C. or at −20° C. The culture supernatants were replaced in the bottles by the same amount of pyrogen-free distilled water to Lyse the cells. The Lysate was recovered, aliquoted and also stored at −20° C. The following experiments were carried out in the presence or absence of interferon-γ ($10^3$ U/ml) at a dose at which IFN-γ alone was inactive.

Tests for the presence in the supernatants of monokines (interleukin-1 and tumor necrosis factor) on the basis of their biological activity.

Interleukin-1 (IL-1) Test:

This test was first described by Gery et al in 1972 [Gery et al, 1972 Potentiation of the T Lymphocyte response to mitogens. II. The Cellular Source of Potentiating Mediator(s). J. Exp. Med., 136–143]. It is based on the co-mitogenic action of IL-1 in the presence of an antigen (mimicked by phytohaemagglutinin in the test) on mouse thymocytes. $1.5 \times 10^6$ thymocytes of C₃H/HeJ mice (supplied by C.S.E.A.L. of Orleans) were cultured for 3 days in the presence of different dilutions of cell supernatants and lysates likely to contain IL-1 activity, and Wellcome PHA-P (1 μg/ml), in culture plates having 96 flat-bottomed wells, in a final volume of 200 μl of medium composed of RPMI 1640 containing, in addition to antibiotics (penicillin 1 γ/ml streptomycin 1000 U/ml , 1 mM HEPES buffer, 2 mM glutamine, 5% calf serum and $5 \times 10^{-5}$M 2-mercaptoethanol. After 68 hours at culturing, 1 μCi of tritiated thymidine was added to each well ([methyl³H]thymidine, CEA Saclay, TMM79A, specific activity 1 μCi/mM), and the radioactivity incorporated by the cells was measured after the cultures had been filtered on a Skaton type semi-automatic collecting apparatus and the filters counted in a scintillation counter (LKB). The results were expressed as the difference between the pulses per minute incorporated by the cultures in the presence of supernatants and the pulses per minute incorporated by the control cultures.

Tumor Necrosis Factor (TNF) Test:

TNF activity was demonstrated by the toxicity of this factor on L-929 target cells (sub-clone α). The technique was sensitized by adding actinomycin D to the test. The L cells were distributed in the proportion of $2 \times 10^4$ cells per well of a flat-bottomed microplate in 100 ul of RPMI 1640 medium enriched with 5% calf serum, glutamine, HEPES buffer and antibiotics. After 24 hours, different dilutions of the test supernatants were added in a volume of 100 μl, as well as a dose of actinomycin D of 1 μg/ml. After 24 hours of culturing, the number of unlysed viable cells was measured by staining the plates with crystal violet and measuring the optical density of different wells on a multiscan reader.

RESULTS

The products of Examples 1 and 2 stimulated monocytes and their IL-1 and TNF production. In addition, there was synergy between the products of Examples 1 and 2 and interferon-γ.

Various modifications of the products and processes of the invention may be made without departing from the spirit or scope thereof and it should be understood that the invention is intended to be limited only as defined in the appended claims.

What we claim is:

1. A compound selected from the group consisting of all isomeric forms and mixtures of isomers of glutamic acid compounds of the formula

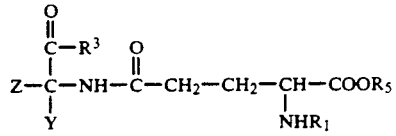

wherein the glutamic acid is of D- or L-configuration, $R_1$ is selected from the group consisting of hydrogen, alkyl or 1 to 5 carbon atoms and an amino acid and an amino acid in which the amine is amidified with an optionally unsaturated aliphatic carboxylic acid of 6 to 24 carbon atoms, or $R_1$ is selected from the group consisting of a residue of $C_6-C_{24}$ optionally unsaturated aliphatic acid, $R_5$ is selected from the group consisting of hydrogen and an alkyl of 1 to 5 carbon atoms, $R_3$ is selected from the group consisting of hydroxy, alkoxy of 1 to 5 carbon toms, an amino acid with the amino optionally substituted with alkyl of 1 to 5 carbon toms, Z is

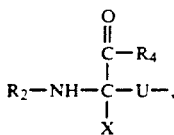

R₂ is selected from the group consisting of hydrogen and an amino acid, R₄ is selected from the group consisting of hydroxy, alkoxy of 1 to 5 carbon toms and an amino acid optionally substituted on the amine with alkyl of 1 to 5 carbon atoms, U is selected from the group consisting of

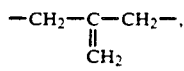

—CH=CH—CH₂— (E or Z isomer), —CH₂—CH= CH— (E or Z isomer) and

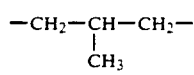

or U and Y together are =CH—CH₂—CH₂— (E or Z isomer) and X is hydrogen or U and X are =CH—CH₂—CH₂— (E or Z isomer) and Y is hydrogen and their salts with non-toxic, pharmaceutically acceptable acid or bases.

2. A compound of claim 1 wherein the glutamic acid has D-configuration.

3. A compound of claim 2 wherein R₃ and R₄ are hydroxy.

4. A compound of claim 2 wherein R₅ is hydrogen.

5. A compound of claim 3 wherein R₅ is hydrogen.

6. A compound of claim 1 selected from the group consisting of 2-amino-6-(γ-D-glutamylamino)-4-methyleneheptanedioic acid and 2-(L-alanylamino)-6-(γ-D-glutamylamino)-4-methyleneheptanedioic acid and their non-toxic, pharmaceutically acceptable addition salts with acids and bases.

7. An immunomodulatory composition comprising an immunomodulatorily effective amount of at least one compound of claim 1 and an inert pharmaceutical carrier.

8. A composition of claim 7 wherein the glutamic acid has D-configuration.

9. A composition of claim 7 wherein the R₃ and R₄ are hydroxy.

10. A composition of claim 7 wherein R₅ is hydrogen.

11. A composition of claim 7 wherein R₅ is hydrogen.

12. A composition of claim 7 wherein the active compound is selected from the group consisting of 2-amino-6-(-D-glutamylamino)4-methyleneheptanedioic acid and 2-(L-alanylamino)-6-(γ-D-glutamylamino)-4-methyleneheptanedioic acid and their non-toxic, pharmaceutically acceptable addition salts with acids and bases.

13. A method of inducing immunomodulatory activity in warm-blooded animals comprising administering to warm-blooded animals an immunomodulatorily effective amount of at least one compound of claim 1.

14. A method of claim 13 wherein the glutamic acid has D-configuration.

15. A method of claim 13 wherein R₃ and R₄ are hydroxy.

16. A method of claim 13 wherein R₅ is hydrogen.

17. A method of claim 13 wherein R₅ is hydrogen.

18. A method of claim 13 wherein the active compound is 2-amino-6-(γ-D-glutamylamino)-4-methyleneheptanedioic acid and 2-(L-alanylamino)-6-(γ-D-glutamylamino)-4-methyleneheptanedioic acid and their non-toxic, pharmaceutically acceptable addition salts with acids and bases.

* * * * *